United States Patent [19]

Stetter et al.

[11] Patent Number: 4,638,004
[45] Date of Patent: Jan. 20, 1987

[54] SUBSTITUTED PHENYLSULPHONYLUREAS

[75] Inventors: Jörg Stetter, Wuppertal; Heinz-Jürgen Wroblowsky, Langenfeld; Robert R. Schmidt, Bergisch-Gladbach; Hans-Joachim Santel, Cologne; Gerd Hänssler, Leverkusen; Klaus Lürssen, Bergisch-Gladbach, all of Fed. Rep. of Germany

[73] Assignee: Bayer Aktiengesellschaft, Leverkusen, Fed. Rep. of Germany

[21] Appl. No.: 734,503

[22] Filed: May 15, 1985

[30] Foreign Application Priority Data

Jun. 4, 1984 [DE] Fed. Rep. of Germany ....... 3420769

[51] Int. Cl.⁴ ................... C07D 239/46; A01N 43/54
[52] U.S. Cl. ........................................ 514/272; 71/92; 544/229; 544/321; 544/332; 514/275
[58] Field of Search ................... 71/92; 544/229, 321, 544/332; 514/275, 272

[56] References Cited

U.S. PATENT DOCUMENTS 4,213,914  7/1980  Bargain et al. ...................... 544/229
4,588,432  5/1986  Hillemann ............................ 544/212

*Primary Examiner*—John M. Ford
*Attorney, Agent, or Firm*—Sprung Horn Kramer & Woods

[57] ABSTRACT

Plant growth-regulating and fungicidally active novel substituted phenylsulphonylureas of the formula

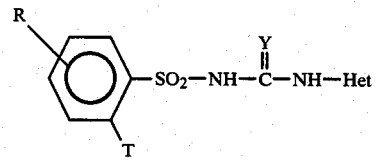

in which R is hydrogen, halogen, alkyl, alkoxy, halogenoalkyl or nitro,
Y is oxygen or sulphur,
Het is

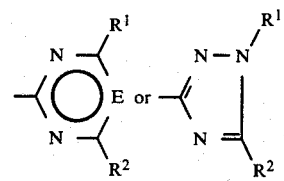

T is $-X-CH_2-Si(CH_3)_3$, or

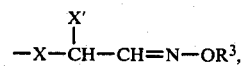

or, if Het is

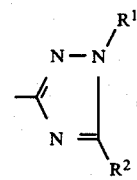

can also be

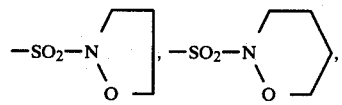

$-O-CH_2-CN$ or $-O-CH_2-CO-CH_3$,
E is nitrogen or CH,
$R^1$ and $R^2$ each independently is alkyl, alkoxy, or alkoxyalkyl,
X is oxygen, sulphur, the sulphinyl group or the sulphonyl group,
X' is hydrogen or alkyl and
$R^3$ is hydrogen, alkyl, alkenyl, alkinyl, halogenoalkyl, halogenoalkenyl, alkoxyalkyl, alkylthioalkyl or optionally substituted aralkyl.

14 Claims, No Drawings

SUBSTITUTED PHENYLSULPHONYLUREAS

The invention relates to new substituted phenylsulphonylureas, several processes for their preparation, and their use as plant-treatment agents, in particular as herbicides, plant growth regulators and fungicides.

It is already known that certain substituted phenylsulphonylureas, such as, for example, N-(2-cyanomethoxyphenylsulphonyl)-N'-(4,6-dimethylpyrimidin-2-yl)-urea, possess herbicidal and plant growth-regulating properties (see, for example, EP-OS (European Published Specification) 85,028). However, the herbicidal and plant growth-regulating properties of these previously known substituted phenylsulphonylureas are not always completely satisfactory in all fields of use, particularly when low amounts and concentrations are used.

Nothing is known to date concerning any fungicidal action of sulphonylureas of this type.

New substituted phenylsulphonylureas of the general formula (I)

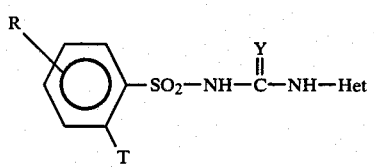

in which
R represents hydrogen, halogen, alkyl, alkoxy, halogenoalkyl or nitro,
Y represents oxygen or sulphur,
Het represents a heterocyclic radical of the formula

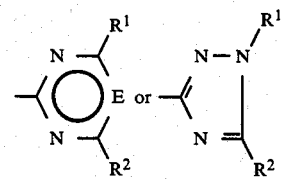

wherein
E represents nitrogen or the CH group and $R^1$ and $R^2$ independently of one another each represent alkyl, alkoxy or alkoxyalkyl, and
T represents one of the radicals —X—CH$_2$—Si(CH$_3$)$_3$ or

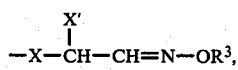

wherein
X in each case represents oxygen, sulphur, the sulphinyl group or the sulphonyl group,
X' represents hydrogen or alkyl and
$R^3$ represents hydrogen, alkyl, alkenyl, alkinyl, halogenoalkyl, halogenoalkenyl, alkoxyalkyl, alkylthioalkyl or optionally substituted aralkyl,
and furthermore represents one of the radicals

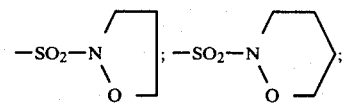

—O—CH$_2$—CN or —O—CH$_2$—CO—CH$_3$, in the case in which Het represents a heterocyclic structure of the formula

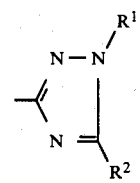

wherein
$R^1$ and $R^2$ have the meaning given above, have been found.

Furthermore, it has been found that the new substituted phenylsulphonylureas of the formula (I) are obtained if (a) heterocyclic amino compounds of the formula (II)

Het—NH$_2$ (II)

in which
Het has the meaning given above, are reacted with phenylsulphonyl iso(thio)cyanates of the formula (III)

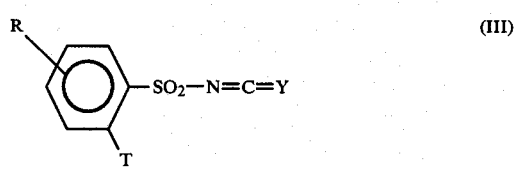

in which
R, Y and T have the meaning given above, if appropriate in the presence of a diluent and, if appropriate, in the presence of a basic catalyst, or if (b) phenylsulphonamides of the formula (IV)

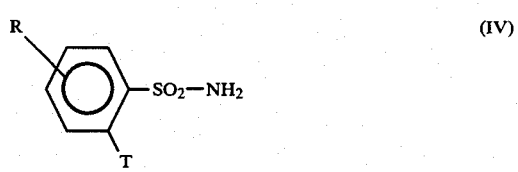

in which
R and T have the meaning given above, are reacted with (thio)carbamates of the formula (V)

in which
Y and Het have the meaning given above and $R^4$ represents alkyl or aryl, if appropriate in the presence of a diluent and, if appropriate, in the presence of an acid-binding agent.

Finally, it has been found that the new substituted phenylsulphonylureas of the formula (I) possess herbicidal properties, in particular selective herbicidal, plant growth-regulating and fungicidal properties. They can therefore be employed as plant-treatment agents. Surprisingly, the new substituted phenylsulphonylureas of the formula (I) exhibit not only a substantially improved herbicidal action against weeds but also a substantially improved selectivity with respect to crop plants compared with the compounds known from the prior art, such as, for example, N-(2-cyanomethoxyphenylsulphonyl)-N'-(4,6-dimethylpyrimidin-2-yl)-urea, which is a similar compound chemically and in terms of its action, and furthermore exhibit valuable plant growth-regulating and fungicidal activities.

Formula (I) gives a general definition of the substituted phenylsulphonylureas according to the invention.

Preferred compounds of the formula (I) are those in which:

R represents hydrogen, fluorine, chlorine, bromine, iodine, nitro or alkyl, halogenoalkyl or alkoxy, each of which is straight-chain or branched and each of which has up to 4 carbon atoms and, where relevant, up to 9 identical or different halogen atoms, Y represents oxygen or sulphur, Het represents a heterocyclic radical of the formula

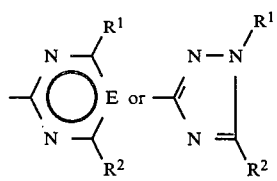

wherein

E represents nitrogen or the CH group and $R^1$ and $R^2$ independently of one another each represent straight-chain or branched alkyl, alkoxy or alkoxyalkyl, each having up to 6 carbon atoms in the individual alkyl parts, and T represents one of the radicals —X—CH$_2$—Si(CH$_3$)$_3$ or

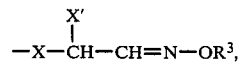

wherein

X in each case represents oxygen, sulphur, the sulphinyl group or the sulphonyl group, X' represents hydrogen or straight-chain or branched alkyl having 1 to 4 carbon atoms and $R^3$ represents hydrogen, or alkyl, alkenyl, alkinyl, alkoxyalkyl, alkylthioalkyl, halogenoalkyl or halogenoalkenyl, each of which is straight-chain or branched and each of which has up to 6 carbon atoms in the individual alkyl or alkenyl or alkinyl parts and, where relevant, up to 9 identical or different halogen atoms, or represents straight-chain or branched aralkyl which has up to 4 carbon atoms in the alkyl part and 6 to 10 carbon atoms in the aryl part and is optionally monosubstituted or polysubstituted in the aryl part by identical or different substituents, suitable substituents being: halogen, cyano, nitro and alkyl, alkoxy or halogenoalkyl, each of which is straight-chain or branched and each of which has up to 4 carbon atoms and, where relevant, up to 9 identical or different halogen atoms, and furthermore represents one of the radicals

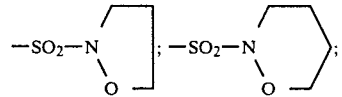

in the case in which Het represents a heterocyclic structure of the formula

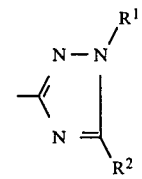

wherein $R^1$ and $R^2$ have the meaning given above.

Particularly preferred compounds of the formula (I) are those in which:

R represents hydrogen, fluorine, chlorine, bromine, nitro, methyl, ethyl, n- or i-propyl, trifluoromethyl, methoxy or ethoxy, Y represents oxygen or sulphur, Het represents a heterocyclic radical of the formula

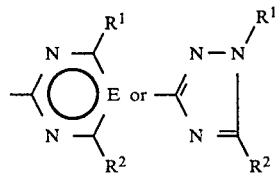

wherein

E represents nitrogen or the CH group and $R^1$ and $R^2$ independently of one another each represent methyl, ethyl, methoxy, ethoxy, methoxymethyl, ethoxymethyl, methoxyethyl or ethoxyethyl, T represents one of the radicals —O—CH$_2$—Si(CH$_3$)$_3$, —S—CH$_2$—Si(CH$_3$)$_3$, —SO$_2$—CH$_2$—Si(CH$_3$)$_3$,

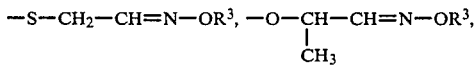

wherein $R^3$ represents hydrogen, methyl, ethyl, n- or i-propyl, n-, i-, s- or t-butyl, allyl, dichloroallyl, butenyl, propargyl, methoxymethyl, methoxyethyl, ethoxyethyl, methylthiomethyl, methylthioethyl or ethylthioethyl, or represents benzyl or phenylethyl, each of which is optionally monosubstituted to trisubstituted in the phenyl part by identical or different substituents from amongst fluorine, chlorine, bromine, cyano, nitro, methyl, ethyl, methoxy, ethoxy and trifluoromethyl, and furthermore represents a radical

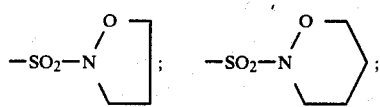

—O—CH₂—CN or —O—CH₂—CO—CH₃ in the case in which Het represents a heterocyclic structure of the formula

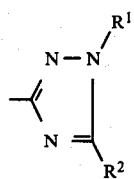

wherein
R¹ and R² have the meaning given above.

In addition to the compounds mentioned in the preparation examples, the following substituted phenylsulphonylureas of the formula (I) may be mentioned individually:

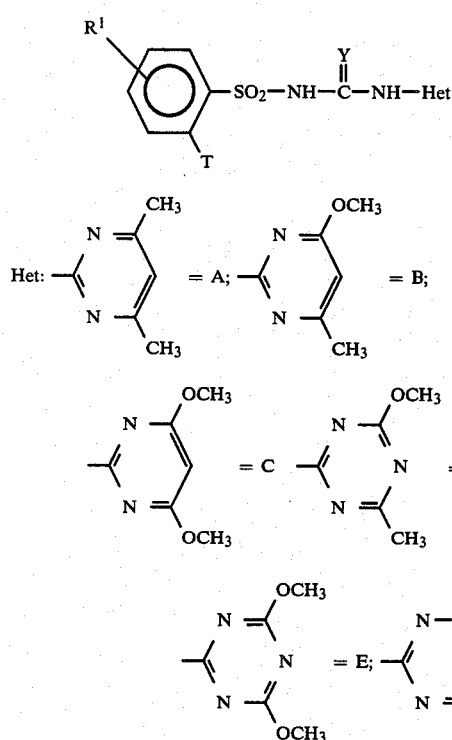

TABLE 1

| R¹ | T | Y | Het |
|---|---|---|---|
| H | (CH₃)₃Si—CH₂—O— | O | A |
| H | (CH₃)₃Si—CH₂—O— | O | C |
| H | (CH₃)₃Si—CH₂—O— | O | D |
| H | (CH₃)₃Si—CH₂—O— | O | E |
| H | (CH₃)₃Si—CH₂—O— | O | A |

TABLE 1-continued

| R¹ | T | Y | Het |
|---|---|---|---|
| H | (CH₃)₃Si—CH₂—O— | S | B |
| H | (CH₃)₃Si—CH₂—O— | S | C |
| H | (CH₃)₃Si—CH₂—O— | S | E |
| H | (CH₃)₃Si—CH₂—O— | S | D |
| H | (CH₃)₃Si—CH₂—O— | O | F |
| H | (CH₃)₃Si—CH₂—O— | S | F |
| H | (CH₃)₃Si—CH₂—S— | O | A |
| H | (CH₃)₃Si—CH₂—S— | O | B |
| H | (CH₃)₃Si—CH₂—S— | O | C |
| H | (CH₃)₃Si—CH₂—S | O | D |
| H | (CH₃)₃Si—CH₂—S— | O | E |
| H | (CH₃)₃Si—CH₂—S— | O | F |
| H | (CH₃)₃Si—CH₂—SO₂— | O | A |
| H | (CH₃)₃Si—CH₂—SO₂— | O | B |
| H | (CH₃)₃Si—CH₂—SO₂— | O | C |
| H | (CH₃)₃Si—CH₂—SO₂— | O | D |
| H | (CH₃)₃Si—CH₂—SO₂— | O | E |
| H | (CH₃)₃Si—CH₂—SO₂— | O | F |
| H | CH₃O—N=CH—CH₂—O— | O | C |
| H | CH₃O—N=CH—CH₂—O— | O | D |
| H | CH₃O—N=CH—CH₂—O— | O | E |
| H | CH₃O—N=CH—CH(CH₃)—O— | O | A |
| H | CH₃O—N=CH—CH(CH₃)—O— | O | B |
| H | CH₃O—N=CH—CH(CH₃)—O— | O | C |
| H | CH₃O—N=CH—CH(CH₃)—O— | O | D |
| H | CH₃O—N=CH—CH(CH₃)—O— | O | E |
| H | CH₃O—N=CH—CH(CH₃)—O— | O | F |
| H | CH₃ON=CH—CH₂—S— | O | A |
| H | CH₃ON=CH—CH₂—S— | O | B |
| H | CH₃ON=CH—CH₂—S— | O | C |
| H | CH₃ON=CH—CH₂—S— | O | D |
| H | CH₃ON=CH—CH₂—S— | O | E |
| H | CH₃O—N=CH—CH(CH₃)—S— | O | A |
| H | CH₃O—N=CH—CH(CH₃)—S— | O | B |
| H | CH₃O—N=CH—CH(CH₃)—S— | O | C |
| H | CH₃O—N=CH—CH₂—SO₂— | O | A |
| H | CH₃O—N=CH—CH₂—SO₂— | O | B |
| H | CH₃O—N=CH—CH₂—SO₂— | O | C |
| H | CH₃O—N=CH—CH₂—SO₂— | O | D |
| H | CH₃O—N=CH—CH₂—SO₂— | O | E |
| H | CH₃O—N=CH—CH₂—SO₂— | O | F |
| H | CH₃O—N=CH—CH(CH₃)—SO₂— | O | A |
| H | CH₃O—N=CH—CH(CH₃)—SO₂— | O | B |

TABLE 1-continued

| R¹ | T | Y | Het |
|---|---|---|---|
| H | CH₃O—N=CH—CH(CH₃)—SO₂— | O | C |
| H | CH₃O—N=CH—CH(CH₃)—SO₂— | O | D |
| H | CH₃O—N=CH—CH₂—O— | S | A |
| H | CH₃O—N=CH—CH₂—O— | S | B |
| H | CH₃O—N=CH—CH₂—O— | S | C |
| H | C₂H₅O—N=CH—CH₂—O— | O | B |
| H | C₂H₅O—N=CH—CH₂—O— | S | B |
| H | C₂H₅O—N=CH—CH₂—O— | O | A |
| H | C₂H₅O—N=CH—CH₂—O— | O | E |
| H | CH₃—CO—CH₂—O— | S | F |
| H | NC—CH₂—O— | S | F |
| H | (tetrahydropyranyl-N—SO₂—) | S | F |
| H | (morpholinyl-N—SO₂—) | S | F |
| H | CH₃(CH₂)₂—O—N=CH—CH₂—O— | O | A |
| H | CH₃(CH₂)₂—O—N=CH—CH₂—O— | O | B |
| H | CH₃(CH₂)₂—O—N=CH—CH₂—O— | O | C |
| H | CH₃(CH₂)₂—O—N=CH—CH₂—O— | O | B |
| H | CH₃(CH₂)₂—O—N=CH—CH₂—O— | S | B |
| H | CH₃(CH₂)₂—O—N=CH—CH₂—O— | O | E |
| H | CH₃(CH₂)₂—O—N=CH—CH₂—O— | S | D |
| H | CH₃=CH—CH₂—O—N=CH—CH₂—O— | O | F |
| H | CH₂=CH—CH₂—O—N=CH—CH₂—O— | S | F |
| H | CH₂=CH—CH₂—O—N=CH—CH₂—O— | O | A |
| H | CH₂=CH—CH₂—O—N=CH—CH₂—O— | O | B |
| H | CH₂=CH—CH₂—O—N=CH—CH₂—O— | O | C |
| H | CH₂=CH—CH₂—O—N=CH—CH₂—O— | O | D |
| H | CH₂=CH—CH₂—O—N=CH—CH₂—O— | O | E |
| H | CH₂=CH—CH₂—O—N=CH—CH₂—O— | O | F |

If, for example, 2-cyanomethoxyphenylsulphonyl isocyanate and 3-amino-5-methoxy-1-methyl-1,2,4-triazole are used as starting materials, the course of the reaction of process (a) according to the invention can be represented by the following equation:

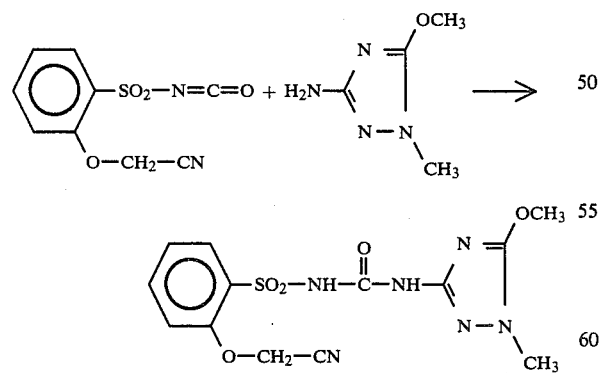

If, for example, 2-[(2-methoximino)-ethoxy]-phenyl-sulphonamide and O-phenyl N-(4-methoxy-6-methyl-pyrimidin-2-yl)-carbamate are used as starting materials, the course of the reaction of process (b) according to the invention can be represented by the following equation:

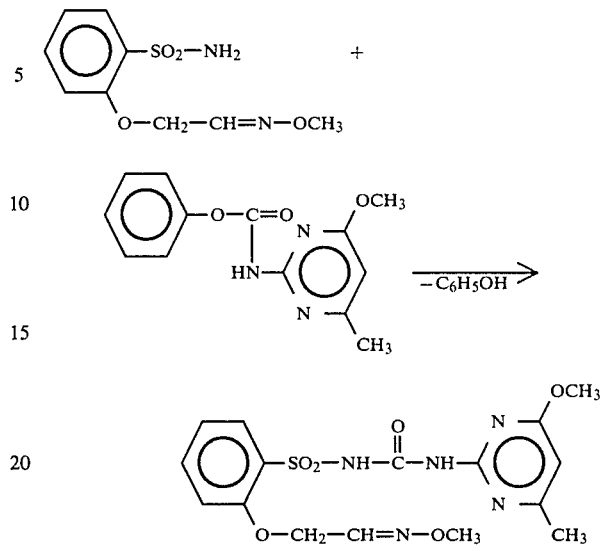

Formula (II) gives a general definition of the heterocyclic amino compounds required as starting materials for carrying out process (a) according to the invention. In this formula (II), Het preferably represents those radicals which have already been mentioned in the description of the substances according to the invention, of the formula (I), as being preferred for these substituents.

The heterocyclic compounds of the formula (II) are known (see, for example, European Pat. No. 73,627, European Pat. No. 73,562, European Pat. No. 85,028 and U.S. Pat. No. 4,127,405).

Formula (III) gives a general definition of the phenylsulphonyl iso(thio)cyanates furthermore required as starting materials for carrying out process (a) according to the invention. In this formula (III), R, Y and T preferably represent those radicals which have already been mentioned in the description of the substances according to the invention, of the formula (I), as being preferred for these substituents.

Some of the phenylsulphonyl iso(thio)cyanates of the formula (III) are known (see, for example, EP-OS (European Published Specification) 85,028). They are obtained when substituted sulphonamides of the formula (IV)

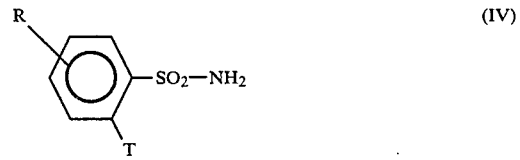

in which
R and T have the meaning given above, are reacted with phosgene or thiophosgene or with chlorosulphonyl isocyanate of the formula (VI)

if appropriate in the presence of a diluent, such as, for example, chloroform or chlorobenzene, and, if appropriate, in the presence of an acid-binding agent, such as, for example, triethylamine, at temperatures between −30° C. and +150° C.

Formula (IV) gives a general definition of the phenylsulphonamides required as starting materials for carrying out process (b) according to the invention and for the preparation of the precursors of the formula (III). In this formula (IV), R and T preferably represent those substituents which have already been mentioned in the description of the substances according to the invention, of the formula (I), as being preferred for these radicals.

Some of the phenylsulphonamides of the formula (IV) are likewise known (see, for example, European Pat. No. 85,028). They are obtained, for example, when 2-hydroxy- or 2-mercaptophenylsulphonamides of the formula (VII)

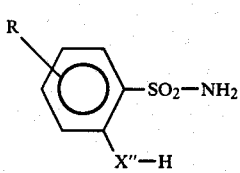

(VII)

in which
R has the meaning given above and
X″ represents oxygen or sulphur, are reacted with substituted halogenoalkyl compounds of the formula (VIII)

T′—Hal          (VIII)

in which
Hal represents halogen, in particular chlorine or bromine, and
T′ represents one of the radicals —CH₂—Si(CH₃)₃, —CH₂—CN, —CH₂—CO—CH₃ or

wherein
$R^3$ and X′ preferably represent those radicals which have already been mentioned in the description of the substances according to the invention, of the formula (I), as being preferred for these substituents,
if appropriate in the presence of a diluent, such as, for example, acetonitrile and, if appropriate, in the presence of an acid-binding agent, such as, for example, potassium carbonate, at temperatures between +20° C. and +120° C., and—in the case in which X″=S— the resulting 2-mercaptophenylsulphonamides of the formula (IVa)

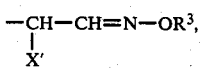

(IVa)

in which
R and T′ have the meaning given above, are, if required, oxidized in a generally customary manner in a 2nd stage with oxidizing agent, for example those of the formula (IX)

H—O—O—$R^5$          (IX)

in which
$R^5$ represents hydrogen or an acyl radical, in particular hydrogen, acetyl, propionyl, benzoyl, 3-chlorobenzoyl or 4-nitrobenzoyl,
if appropriate in the presence of a diluent, such as, for example, acetone and, if appropriate, in the presence of a catalyst, such as, for example, ammonium molybdate, at temperatures between −30° C. and +50° C., to give the corresponding sulphinyl or sulphonyl compounds of the formula (IVb)

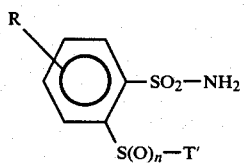

(IVb)

in which
T′ has the meaning given above and
n represents 1 or 2.
Compounds of the formula (IVc)

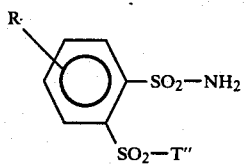

(IVc)

in which
R has the meaning given above and
T″ represents a heterocyclic structure of the formula

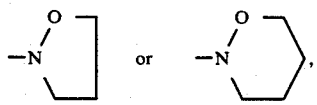

are obtained if 2-chlorosulphonylphenylsulphonyl fluorides of the formula (X)

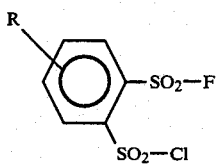

(X)

in which
R has the meaning given above, are first reacted, in a 1st stage, with heterocycles of the formula (XI)

H—T″          (XI)

in which
T″ has the meaning given above,
if appropriate in the presence of a diluent, such as, for example, toluene, and, if appropriate, in the presence of an acid-binding agent, such as, for example, triethylamine, at temperatures between −20° C. and +40° C., and the resulting sulphonyl fluorides of the formula (XII)

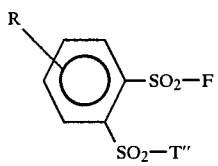

in which

R and T″ have the meaning given above. are reacted, in a 2nd stage, with ammonia or aqueous ammonium hydroxide at temperatures between +20° C. and +60° C.

Formula (V) gives a general definition of the (thio)-carbamates furthermore required as starting materials for carrying out process (b) according to the invention. In this formula (V), Y and Het preferably represent those substituents which have already been mentioned in the description of the substances according to the invention, of the formula (I), as being preferred for these radicals. $R^4$ preferably represents methyl, ethyl or phenyl.

The (thio)carbamates of the formula (V) are known (see, for example, European Pat. Nos. 70,802, 70,804, 71,958, 72,347 or 79,683) or can be prepared by known methods by simple analogous processes.

Chlorosulphonyl isocyanate of the formula (VI), 2-hydroxyphenylsulphonamides of the formula (VII), substituted halogenoalkyl compounds of the formula (VIII), 2-chlorosulphonylphenylsulphonyl fluorides of the formula (X) and heterocycles of the formula (XI) are generally known compounds of organic chemistry, or can be prepared by generally known processes in a simple analogous manner.

Preferred diluents for carrying out processes (a) and (b) according to the invention are inert organic solvents.

These include, in particular, optionally halogenated aliphatic or aromatic hydrocarbons, such as, for example, benzine, benzene, toluene, xylene, chlorobenzene, petroleum ether, hexane, cyclohexane, dichloromethane, chloroform or carbon tetrachloride, ethers, such as diethyl ether, dioxane, tetrahydrofuran or ethylene glycol dimethyl or diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric acid triamide, esters, such as ethyl acetate, or sulphoxides, such as dimethylsulphoxide.

Processes (a) and (b) according to the invention can, if appropriate, be carried out in the presence of a basic catalyst.

Suitable catalysts are all customary inorganic or organic bases. These include, for example, alkali metal hydroxides, such as sodium hydroxide or potassium hydroxide, alkali metal carbonates, such as sodium carbonate, potassium carbonate or sodium bicarbonate, and tertiary amines, such as triethylamine, N,N-dimethylaniline, pyridine, N,N-dimethylaminopyridine, diazabicyclooctane (DABCO), diazabicyclononene (DBN) or diazobicycloundecene (DBU).

In carrying out processes (a) and (b) according to the invention, the reaction temperatures can be varied within a relatively wide range. In general, the reaction is carried out at temperatures between −20° C. and +120° C., preferably at temperatures between 0° C. and +50° C.

To carry out process (a) according to the invention, in general 1.0 to 1.5 mols preferably 1.0 to 1.2 mols, of phenylsulphonyl iso(thio)cyanate of the formula (III) and, if appropriate, 0.01 to 1.0 mol, preferably 0.1 to 1.0 mol, of basic catalyst are employed per mol of the heterocyclic amino compound of the formula (II).

To carry out process (b) according to the invention, in general 1.0 to 1.5 mols, preferably 1.0 to 1.2 mols, of the (thio)carbamate of the formula (V) and, if appropriate, 0.01 to 1.0 mol, preferably 0.1 to 1.0 mol, of basic catalyst are employed per mol of the phenylsulphonamide of the formula (IV).

In both preparation processes (a) and (b), working up and isolation of the end products of the formula (I) are carried out in a customary manner.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera

Spinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduss, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera

Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera

Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera

Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hop fields, and for the selective combating of weeds in annual cultures.

The active compounds according to the invention exhibit not only a substantially improved herbicidal activity against important weeds but also substantially improved toleration by important crop plants, and can therefore be employed as selective weedkillers, for example in cereals.

The active compounds which can be used according to the invention engage in the metabolism of the plants and can therefore also be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

Plant growth-regulating compounds can be employed, for example, to inhibit vegetative growth of the plants. Such inhibition of growth is inter alia of economic interest in the case of grasses, since is is thereby possible to reduce the frequency of cutting the grass in ornamental gardens, parks and sports grounds, at verges, at airports or in fruit orchards. The inhibition of growth of herbaceous and woody plants at verges and in the vicinity of pipelines or overland lines or, quite generally, in areas in which heavy additional growth of plants is undesired, is also of importance.

The use of growth regulators to inhibit the growth in length of cereals is also important. The danger of lodging of the plants before harvesting is thereby reduced or completely eliminated. Furthermore, growth regulators can strengthen the stem of cereals, which again counteracts lodging. Use of growth regulators for shortening and strengthening the stem enables higher amounts of fertilizer to be applied to increase the yield, without danger of the cereal lodging.

In the case of many crop plants, inhibition of the vegetative growth makes denser planting possible, so that greater yields per area of ground can be achieved. An advantage of the smaller plants thus produced is also that the crop can be worked and harvested more easily.

Inhibition of the vegetative growth of plants can also lead to increases in yield, since the nutrients and assimilates benefit blossoming and fruit formation to a greater extent than they benefit the vegetative parts of plants.

Promotion of vegetative growth can also frequently be achieved with growth regulators. This is of great utility if it is the vegetative parts of the plants which are harvested. Promoting the vegetative growth can, however, also simultaneously lead to a promotion of generative growth, since more assimilates are formed, so that more fruit, or larger fruit, is obtained.

Increases in yield can in some cases be achieved by affecting the plant metabolism, without noticeable changes in vegetative growth. A change in the composition of plants, which in turn can lead to a better quality of the harvested products, can furthermore be achieved with growth regulators. Thus it is possible, for example, to increase the content of sugar in sugar beet, sugar cane, pineapples and citrus fruit or to increase the protein content in soy beans or cereals. Using growth regulators it is also possible, for example, to inhibit the degradation of desired constituents, such as, for example, sugar in sugar beet or sugar cane, before or after harvesting. It is also possible favorably to influence the production or the efflux of secondary plant constituents. The stimulation of latex flux in rubber trees may be mentioned as an example.

Parthenocarpous fruit can be formed under the influence of growth regulators. Furthermore, the gender of the flowers can be influenced. Sterility of the pollen can also be produced, which is of great importance in the breeding and preparation of hybrid seed.

Branching of plants can be controlled by using growth regulators. On the one hand, by breaking the apical dominance, the development of side shoots can be promoted, which can be very desirable, especially in the cultivation of ornamental plants, also in connection with growth inhibition. On the other hand, however, it is also possible to inhibit the growth of side shoots. There is great interest in this action, for example, in the cultivation of tobacco or in the planting of tomatoes.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The shedding of fruit can also be controlled with growth regulators. On the one hand, it is possible to prevent premature shedding of fruit. However, on the other hand, shedding of fruit, or even the fall of blossom, can be promoted up to a certain degree (thinning out) in order to interrupt the alternance. By alternance there is understood the peculiarity of some varieties of fruit to produce very different yields from year to year, for endogenous reasons. Finally, using growth regulators it is possible to reduce the force required to detach the fruit at harvest time so as to permit mechanical harvesting or facilitate manual harvesting.

Using growth regulators, it is furthermore possible to achieve an acceleration or retardation of ripening of the harvest product, before or after harvesting. This is of particularly advantage, since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators, it is furthermore possible to influence the latent period of speeds or buds of plants, so that the plants, such as, for example, pineapple or ornamental plants in nurseries, germinate, shoot or blossom at a time at which they normally show no readiness to do so. Retarding the shooting of buds or the germination of seeds with the aid of growth regulators can be desirable in regions where frost is a hazard, in order to avoid damage by late frosts.

Finally, the resistance of plants to frost, drought or a high salt content in the soil can be induced with growth regulators. Cultivation of plants in regions which are usually unsuitable for this purpose thereby becomes possible.

The active compounds according to the invention also exhibit a powerful microbicidal action and, when used in appropriate amounts, can also be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

The active compounds according to the invention can be used with particularly good success for combating rice diseases, such as, for example, against the blast disease of rice causative organism (*Pyricularia oryzae*) or against Oomycetes. The active compounds according to the invention exhibit not only an outstanding protective activity but also a very good systemic action.

The active compounds can be converted to the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is liquid solvents and/or solid carriers, optionally with the use of surface-active agents, that is emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strong polar solvents, such as dimethylformamide and dimethylsulphoxide, as well as water; by liquefied gaseous extenders or carriers are meant liquids which are gaseous at normal temperatures and under normal pressure, for example aerosol propellants, such as halogenated hydrocarbons, as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkylsulphates, arylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs such as alizarin dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixing being possible.

Known herbicides, such as, for example, 1-amino-6-ethylthio-3-(2,2-dimethylpropyl)-1,3,5-triazine-2,4-(1H,3H)-dione or N-(2-benzothiazolyl)-N,N'-dimethylurea for combating weeds in cereals; 4-amino-3-methyl-6-phenyl-1,2,4-triazin-5(4H)-one for combating weeds in sugar beet and 4-amino-6-(1,1-dimethylethyl)-3-methylthio-1,2,4-triazin-5-(4H)-one for combating weeds in soy beans, can be used for the mixtures. Mixtures with N,N-dimethyl-N'-(3-trifluoromethylphenyl)-urea, N,N-dimethyl-N'-(3-chloro-4-methylphenyl)-urea, N,N-dimethyl-N'-(4-isopropylphenyl)-urea, 4-amino-6-t-butyl-3-ethyl-thio-1,2,4-triazin-5(4H-one, 2,4-dichlorophenoxyacetic acid, 2,4-dichlorophenoxypropionic acid, (2-methyl-4-chlorophenoxy)-acetic acid, (4-chloro-2-methyl-phenoxy)-propionic acid, 2-benzyloxyethyl, trimethylsilylmethyl or 2,2-diethoxy-ethyl 2-[4-(3,5-dichloropyrid-2-yloxy)-phenoxy]-propionate or other diphenyl ethers are also possible. Surprisingly, some mixtures also show a synergistic action.

Mixtures with other known active compounds, such as fungicides, insecticides, acaricides, nematicides, bird repellents, plant nutrients and agents which improve soil structure, are also possible.

When used as herbicides, the active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 0.001 and 10 kg of active compound per hectare of soil surface, preferably between 0.05 and 5 kg per ha.

When used as plant growth regulators, the active compounds according to the invention can be present in the formulations as a mixture with other known active compounds, such as fungicides, insecticides, acaricides and herbicides, and also as mixtures with fertilizers and other growth regulators.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomizing, scattering, dusting, foaming, coating and the like. Furthermore, it is possible to apply the active compounds in accordance with the ultralow volume process or to inject the active compound preparation or the active compound itself into the soil. It is also possible to treat the seeds of plants.

When the compounds are used as plant growth regulators, the amounts applied can be varied within a substantial range. In general, 0.001 to 10 kg, preferably 0.05 to 5 kg, of the active compound are employed per hectare of soil surface.

As regards the time of application, the rule is that the growth regulators are applied within a preferred period of time, the exact definition of which depends on the climatic and vegetative circumstances.

When the active compounds according to the invention are used as fungicides, they can be present in the formulations or in the various use forms as a mixture with other known active compounds, such as fungicides, bactericides, insecticides, acaricides, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporising, injecting, forming a slurry, brushing on, dusting, scattering, dry dressing, moist dressing, wet dressing, slurry dressing or encrusting.

In the treatment of parts of plants, the active compound concentrations in the use forms can be varied within a wide range. They are, in general, between 1 and 0.0001% by weight, preferably between 0.5 and 0.001% by weight.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight are required at the place of action.

The examples which follow serve to illustrate the invention further.

PREPARATION EXAMPLES

Example 1

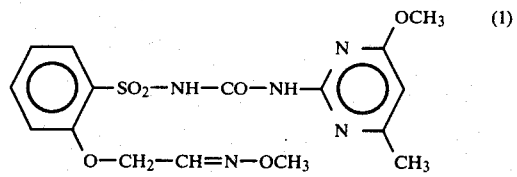

(Process a)

3.2 g (0.02 mol) of diazabicycloundecene (DBU) are added to a stirred mixture of 4.9 (0.02 mol) of 2-(2-methoximino-ethoxy)-phenylsulphonamide and 5.2 g (0.02 mol) of O-phenyl N-(4-methoxy-6-methyl-pyrimidin-2-yl)-carbamate in 160 ml of acetonitrile, and stirring is continued for a further 16 hours at room temperature. For working up the reaction mixture, it is poured into 600 ml of water, acidified with hydrochloric acid and extracted with 500 ml of ethyl acetate, the combined organic phases are washed with water and dried over sodium sulphate, and the solvent is removed in vacuo. The oily residue crystallizes after being triturated with ethyl acetate. 3 g (37% of theory) of N-[2-(2-methoximinoethoxy)-phenylsulphonyl]-N'-(4-methoxy-6-methyl-pyrimidin-2-yl)-urea of melting point 191° C. are obtained.

Preparation of the precursor

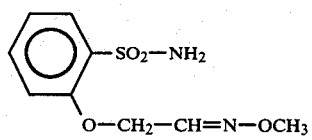

30 g (0.2 mol) of potassium carbonate are introduced into a stirred solution of 18 g (0.1 mol) of 2-hydroxybenzenesulphonamide in 20 ml of acetonitrile. 11 g (0.1 mol) of 1-chloro-2-methoxyiminoethane are then rapidly added dropwise, and the mixture is heated at the boiling point for a further 3 hours. The precipitate which separates out is filtered off under suction, in filtrate is evaporated down, the oily residue is triturated with water, and the product is filtered off under suction and dried on clay. 14 g (57% of theory) of 2-(2-methoxyiminoethoxy)phenylsulphonamide of melting point 103° to 105° C. are obtained.

Example 2

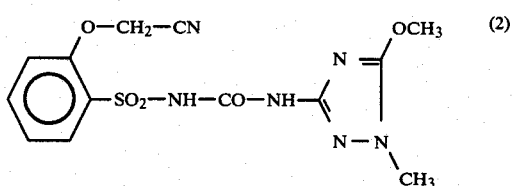

(Process b)

4.8 g (0.03 mol) of diazabicycloundecene (DBU) are added to a stirred suspension of 6.4 g (0.03 mol) of 2-cyanomethoxybenzenesulphonamide and 7.5 g (0.03 mol) of O-phenyl N-(5-methoxy-1-methyl-1,2,4-triazol-3-yl)-carbamate in 80 ml of acetonitrile and, when the addition is complete, stirring is continued for a further 20 hours at room temperature. To work up the reaction mixture, it is poured into water, acidified with hydrochloric acid and extracted with 500 ml of ethyl acetate, and the combined organic phases are dried over sodium sulphate and evaporated down in vacuo. The oily residue crystallizes when triturated with ethyl acetate.

7.8 g (71% of theory) of N-(2-cyanomethoxyphenyl-sulphonyl)-N'-(5-methoxy-1-methyl-1,2,4-triazol-3-yl)-urea of melting point 205° to 207° C. are obtained.

Preparation of the precursor

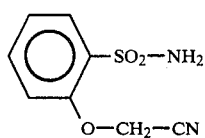

8 g (0.1 mol) of chloroacetonitrile are added dropwise to a stirred suspension of 18 g (0.1 mol) of 2-hydroxybenzenesulphonamide and 15 g (0.1 mol) of potassium carbonate in 250 ml of acetonitrile, and stirring is continued for a further 16 hours at 55° C. to 60° C. when the addition is complete. The reaction mixture obtained is filtered under suction, and the residue is evaporated down and triturated with water. The solid obtained is dried on clay. 14 g (66% of theory) of 2-cyanomethoxy-phenylsulphonamide of melting point 184° to 185° C. are obtained.

The following compounds of the general formula (I) are obtained in a corresponding manner and in accordance with the general preparation data:

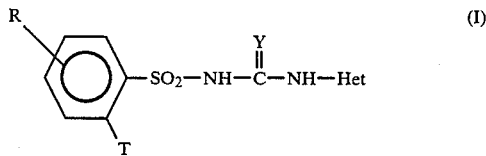

TABLE 2

| Example | R | T | Y | Het | Melting point |
|---|---|---|---|---|---|
| 3 | H | (CH$_3$)$_3$SiCH$_2$—O— | O | ![het]OCH$_3$, pyrimidine with N, N, CH$_3$ | 100–110° C. |
| 4 | H | CH$_3$O—N=CHCH$_2$O— | O | ![het]CH$_3$, pyrimidine with N, N, CH$_3$ | 196° C. |

TABLE 2-continued

| Example | R | T | Y | Het | Melting point |
|---|---|---|---|---|---|
| 5 | H | [5-membered ring]N—SO$_2$— | O | ![het]OCH$_3$, triazole with N=, N—N, CH$_3$ | 202° C. |
| 6 | H | [6-membered ring]N—SO$_2$— | O | ![het]OCH$_3$, triazole with N=, N—N, CH$_3$ | 197° C. |
| 7 | H | CH$_3$—CO—CH$_2$—O— | O | ![het]OCH$_3$, triazole with N=, N—N, CH$_3$ | 172–174° C. |

Use examples

In the use examples below, the compounds listed below are employed as comparison substances:

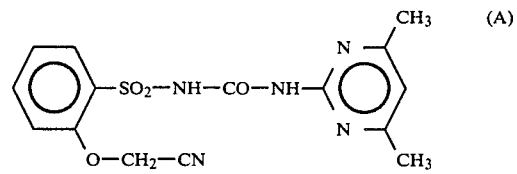 (A)

N-(2-Cyanomethoxyphenylsulphonyl)-N'-(4,6-dimethyl-pyrimidin-2-yl)-urea (disclosed in European Pat. No. 85,028)

$(CH_3—CH_2—CH_2—CH_2—S)_3P=O$ (B)

S,S,S-Tributyl thiophosphate (disclosed in U.S. Patent Specification No. 3,089,807)

$Cl—CH_2—CH_2—N(CH_3)_3{}^{\oplus}Cl^{\ominus}$ (C)

Trimethyl-2-chloroethyl-ammonium chloride (disclosed in DE-AS (German Published Specification) 1,294,734).

 (D)

Maleic hydrazide (disclosed in French Pat. No. 1,397,521; C.A. 63, 4212a (1965))

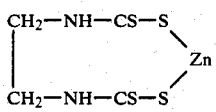

Zinc ethylene-1,2-bis(dithiocarbamate) (disclosed in Phytopathology 33, 1113 (1943))

Example A

Post-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated.

In this test, a clearly superior activity as well as a clearly superior selectivity with respect to crop plants in comparison with the prior art is shown, for example, by the compound according to preparation Example 4.

Example B

Defoliation and desiccation of the leaves of cotton
Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Cotton plants are grown in a greenhouse until the 5th secondary leaf has unfolded completely. In this stage, the plants are sprayed with the preparations of active compound until dripping wet. After 1 week, the shedding of leaves and the desiccation of the leaves are rated, in comparison with the control plants.

In this test, a clearly superior activity compared with the prior art is shown, for example, by the compound according to preparation Example 1.

Example C

Inhibition of growth of barley
Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Barley plants are grown in a greenhouse to the 2-leaf stage. In this stage, the plants are sprayed with the preparations of active compound until dripping wet. After 3 weeks, the additional growth is measured on all plants and the inhibition of growth in percent of the additional growth of the control plants is calculated.

In this test, a clearly superior activity compared with the prior art is shown, for example, by the compounds according to the following preparation Examples: 1, 4 and 7.

Example D

Inhibition of growth of grass (*Festuca pratensis*)
Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Grass (*Festuca pratensis*) is grown in a greenhouse up to a height in growth of 5 cm. In this stage, the plants are sprayed with the preparations of active compound until dripping wet. After 3 weeks, the additional growth is measured and the inhibition of growth in percent of the additional growth of the control plants is calculated.

In this test, a clearly superior activity compared with the prior art is shown, for example, by the compounds according to the following preparation Examples: 1 and 4.

Example E

Pyricularia test (rice)/protective
Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier to the desired concentration.

To test for protective activity, young rice plants are sprayed with the preparation of active compound until dripping wet. After the spray coating has dried on, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation.

In this test, a clearly superior activity compared with the prior art is shown, for example, by the compounds according to the following preparation Examples: 1, 4 and 7.

Example F

Pyricularia test (rice)/systemic
Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier to the desired concentration.

To test for systemic properties, standard soil in which young rice plants have been grown is watered with 40 ml of the preparation of active compound. 7 days after the treatment, the plants are inoculated with an aqueous spore suspension of *Pyricularia oryzae*. Thereafter, the plants remain in a greenhouse at a temperature of 25° C.

and a relative atmospheric humidity of 100% until they are evaluated.

Evaluation of the disease infestation is carried out 4 days after the inoculation.

In this test, a clearly superior activity compared with the prior art is shown, for example, by the compounds according to the following preparation Examples: 1, 2, 4 and 7.

It will be understood that the specification and examples are illustrative but not limitative of the present invention and that other embodiments within the spirit and scope of the invention will suggest themselves to those skilled in the art.

We claim:

1. A substituted phenylsulphonylurea of the formula

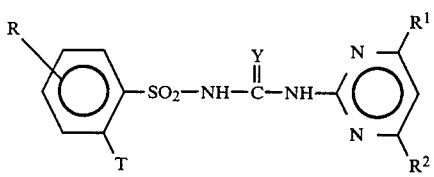

in which
R is hydrogen, fluorine, chlorine, bromine, iodine, nitro or alkyl, halogenoalkyl or alkoxy, each of which has up to 4 carbon atoms and, where relevant, up to 9 halogen atoms,
Y is oxygen or sulphur,
T is $-X-CH_2-Si(CH_3)_3$, or

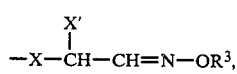

$R^1$ and $R^2$ each independently is alkyl, alkoxy, or alkoxyalkyl, each having up to 6 carbon atoms in the individual alkyl parts,
X is oxygen, sulphur, the sulphinyl group or the sulphonyl group,
X' is hydrogen or alkyl having 1 to 4 carbon atoms, and
$R^3$ is hydrogen, or alkyl, alkenyl, alkinyl, alkoxyalkyl, alkylthioalkyl, halogenoalkyl or halogenoalkenyl, each of which has up to 6 carbon atoms in the individual alkyl or alkenyl or alkinyl parts, and, where relevant, up to 9 halogen atoms, or is aralkyl which has up to 4 carbon atoms in the alkyl part and 6 to 10 carbon atoms in the aryl part and is optionally substituted in the aryl part by halogen, cyano, nitro, or alkyl, alkoxy or halogenoalkyl, each of which has up to 4 carbon atoms and, where relevant, up to 9 halogen atoms.

2. A compound according to claim 1, in which:
R is hydrogen, fluorine, chlorine, bromine, nitro, methyl, ethyl, n- or i-propyl, trifluoromethyl, methoxy or ethoxy,
$R^1$ and $R^2$ each independently is methyl, ethyl, methoxy, ethoxy, methoxymethyl, ethoxymethyl, methoxyethyl or ethoxyethyl,
T is $-O-CH_2-Si(CH_3)_3$, $-S-CH_2-Si(CH_3)_3$, $-SO_2-CH_2-Si(CH_3)_3$, $-S-CH_2-CH=N-OR^3$,

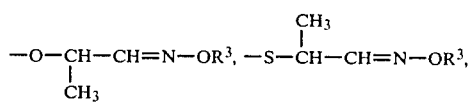

$-O-CH_2-CH=N-OR^3$, $R^3$ is hydrogen, methyl, ethyl, n- or i-propyl, n-, i-, s- or t-butyl, allyl, dichloroallyl, butenyl, propargyl, methoxymethyl, methoxyethyl, ethoxyethyl, methylthiomethyl, methylthioethyl or ethylthioethyl, or is benzyl or phenylethyl, each of which is optionally monosubstituted or trisubstituted in the phenyl part by fluorine, chlorine, bromine, cyano, nitro, methyl, ethyl, methoxy, ethoxy and/or trifluoromethyl.

3. A compound according to claim 1, wherein such compound is N-[2-(methoximinoethoxy)-phenylsulphonyl]-N'-(4-methoxy-6-methyl-pyrimidin-2-yl)-urea of the formula

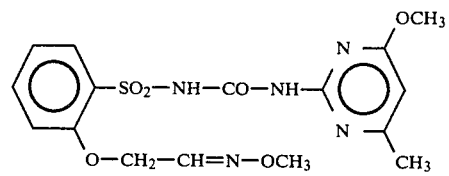

4. A compound according to claim 1, wherein such compound is N-(2-trimethylsilylmethoxy-phenylsulphonyl)-N'-(4-methoxy-6-methyl-pyrimidin-2-yl)-urea of the formula

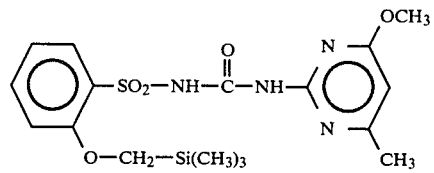

5. A compound according to claim 1, wherein such compound is N-[2-(2-methoximinoethoxy)-phenylsulphonyl]-N'-(4,6-dimethyl-pyrimidin-2-yl)-urea of the formula

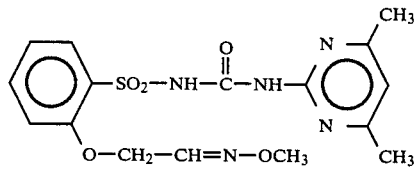

6. A plant growth-regulating or fungicidal composition comprising a plant growth-regulating or fungicidally effective amount of a compound according to claim 1 in admixture with a diluent.

7. A method of regulating the growth of plants which comprises applying to such plants or to a locus in which such plants are grown a plant growth-regulating effective amount of a compound according to claim 1.

8. The method according to claim 7, wherein such compound is
N-[2-(methoximinoethoxy)-phenylsulphonyl]-N'-(4-methoxy-6-methyl-pyrimidin-2-yl)-urea.

9. The method according to claim 7, wherein such compound is

N-(2-trimethylsilylmethoxy-phenylsulphonyl)-N'-(4-methoxy-6-methyl-pyrimidin-2-yl)-urea.

10. The method according to claim 7, wherein such compound is

N-[2-(2-methoximinoethoxy)-phenylsulphonyl]-N'-(4,6-dimethyl-pyrimidin-2-yl)-urea.

11. A method of combating fungi which comprises applying to such fungi or a fungus habitat a fungicidally effective amount of a compound according to claim 1.

12. The method according to claim 11, wherein such compound is

N-[2-(methoximinoethoxy)-phenylsulphonyl]-N'-(4-methoxy-6-methyl-pyrimidin-2-yl)-urea.

13. The method according to claim 11, wherein such compound is

N-(2-trimethylsilylmethoxy-phenylsulphonyl)-N'-(4-methoxy-6-methyl-pyrimidin-2-yl)-urea.

14. The method according to claim 11, wherein such compound is

N-[2-(2-methoximinoethoxy)-phenylsulphonyl]-N'-(4,6-dimethyl-pyrimidin-2-yl)-urea.

* * * * *

UNITED STATES PATENT AND TRADEMARK OFFICE
CERTIFICATE OF CORRECTION

PATENT NO. : 4,638,004

DATED : January 20, 1987

INVENTOR(S) : Jörg Stetter, et al.

It is certified that error appears in the above-identified patent and that said Letters Patent is hereby corrected as shown below:

Col. 4, line 10      After second ";" add -- $-O-CH_2-CN$ or $-O-CH_2-CO-CH_3$ --

Col. 10, line 1      After "oxidizing" delete "agent" and substitute --agents--

Col. 12, line 32      Before "lepidium" delete "Spinapis," and substitute --Sinapis,--

Col. 18, line 44      Before "are" delete "methoxyiminoethane" and substitute --methoximinoethane--

Col. 18, line 47      After "suction," delete "in" and substitute --the--

Col. 18, lines 50 and 51      After "(2-" delete "methoxyiminoethoxy)phenylsulphonamide" and substitute --methoximinoethoxy)-phenylsulphonamide --.

Signed and Sealed this

Twenty-fourth Day of May, 1988

Attest:

DONALD J. QUIGG

Attesting Officer      Commissioner of Patents and Trademarks